United States Patent [19]
Shonfeld et al.

[11] Patent Number: 5,891,104
[45] Date of Patent: Apr. 6, 1999

[54] HYPODERMIC SYRINGE HAVING RETRACTABLE NEEDLE

[75] Inventors: David Shonfeld, Great Neck; Joel Schoenfeld, Woodbury, both of N.Y.

[73] Assignee: Univec, Inc., Garden City, N.Y.

[21] Appl. No.: 782,040

[22] Filed: Jan. 10, 1997

[51] Int. Cl.⁶ .................................................. A61M 5/32
[52] U.S. Cl. ........................................... 604/195; 604/232
[58] Field of Search ..................... 604/110, 187, 604/193, 194, 195, 218, 232, 262, 220, 228

[56] References Cited

U.S. PATENT DOCUMENTS

| | | | |
|---|---|---|---|
| 4,834,717 | 5/1989 | Haber et al. | 604/193 |
| 5,120,311 | 6/1992 | Sagstetter et al. | 604/110 |
| 5,324,272 | 6/1994 | Smedley et al. | 604/193 |
| 5,445,620 | 8/1995 | Haber et al. | 604/232 |
| 5,514,107 | 5/1996 | Haber et al. | 604/232 X |

*Primary Examiner*—John D. Yasko
*Attorney, Agent, or Firm*—Levisohn, Lerner, Berger & Langsam

[57] ABSTRACT

An economical hypodermic syringe is provided. A retractable needle head is provided to slide along longitudinal grooves in the barrel of the syringe. Notches in the grooves engage teeth provided on tabs of the needle head, and lock the needle head in a predetermined position. The tabs are resilient, and if squeezed against the resilient bias, will disengage from the notches in the grooves. In this way, the needle may be partially or fully withdrawn into the barrel. In addition or alternatively, a needle cover is included which is adapted to serve as the plunger of the syringe. The outer diameter of the needle cover is narrower than the inner diameter of both the barrel and an ampoule.

17 Claims, 5 Drawing Sheets

HYPODERMIC SYRINGE HAVING RETRACTABLE NEEDLE

BACKGROUND OF THE INVENTION

1. Field of the Invention

This invention relates to hypodermic syringes.

2. Description of the Related Art

Plastic hypodermic syringes are mass-producible, and are intended to be sterilized or discarded after only one use to prevent the spread of blood-borne diseases such as hepatitis and AIDS from one user to the next. For example, if an individual using a syringe is carrying a blood-borne disease, a subsequent user of the syringe or a person inadvertently stuck with the needle runs a great risk of contracting the disease.

Plastic hypodermic syringes which are not pre-filled are usually loaded by the action of a reciprocable plunger which creates a reduced pressure in the barrel and results in the intake of fluid (medication) into the barrel. Such syringes depend on a rubber seal attached to the plunger to insure that a reduced pressure can be effected because of the wider tolerances experienced in plastic molding, in contrast to precisely ground glass syringes which do not require a seal. Withdrawal of the plunger with seal attached is now messy since the seal has been covered with fluid. Also, the syringe requires a separate needle cover to protect individuals from accidental and potentially hazardous puncture wounds and inadvertent disease transmission. Separate needle covers drive up the cost of the unit.

There is another type of conventional syringe that can be used with pre-filled ampoules. The syringe is provided with a needle having points at both ends, where one end of the needle extends into the barrel of the syringe. When an ampoule is inserted into the barrel, the internal point of the needle punctures the seal of the ampoule, and medicine is placed in fluid communication with the needle. Thereafter, a plunger is placed in the open end of the barrel; when the plunger is depressed, it forces down the stopper of the ampoule, which forces medicine out of the ampoule and through the needle.

There is a drawback to this type of syringe as well. Typically, the needle extends into the barrel (and thus into an inserted ampoule) so much that a significant distance exists between the fluid entry point of the opening in the needle and the bottom of the ampoule. As a result, any medicine in the ampoule below the point of the opening in the needle will not be forced out of the ampoule when the plunger is fully depressed. This "dead space" created at the bottom of the ampoule wastes medicine.

Moreover, typical syringes possess a needle mounted in the bottom wall of a barrel. The amount the needle extends from the barrel is fixed, and may not be altered. This reduces the flexibility of the use of the syringe, as some injections are supposed to be made deeper into the tissue of the patient than others (i.e., intramuscular injections are usually deeper than intravenous injections). Accidents may occur when performing an injection that is meant to be close to the surface of the skin, such as inadvertent extra penetration and related tissue damage.

SUMMARY OF THE INVENTION

It is an object of the present invention to provide a hypodermic syringe that can be used efficiently with pre-filled ampoules of various sizes.

It is another object of the invention to provide an inexpensive reusable hypodermic syringe.

It is still another object of the invention to provide an inexpensive hypodermic syringe that prevents accidental needle sticks and thus disease transmission.

It is yet another object of the invention to provide a hypodermic syringe that can be used with pre-filled ampoules and does not waste medicine.

It is another object of the invention to provide a hypodermic syringe that can be used for a variety of different types of injections that may prevent tissue damage.

The above and other objects are satisfied by the present invention. The invention includes a single use hypodermic syringe having a barrel that can receive an ampoule. A needle head is movably mounted in the barrel and is adapted to move along the barrel. A needle having an axial bore is provided in communication with the interior of the barrel. One end of the needle may preferably extend into the interior portion of the barrel through a bottom wall of the needle head so that the interior bevel of the needle extends only partially into the barrel; when the needle is piercing the rubber seal of a loaded ampoule, dead space is avoided and wasted medicine is reduced.

The barrel is preferably provided with at least one longitudinal groove along which the needle head may slide. Tabs, preferably resilient tabs, extend outward from the needle head and are disposed in the grooves of the barrel. Projections on the tabs, or teeth, engage notches formed in the grooves of the barrel. When the teeth of the tabs are engaged by the notches, the needle head is prevented from sliding along the barrel. By squeezing the tabs in an inward direction, the teeth are disengaged from the notches, and the needle head may slide freely.

A separate notch may be provided at the proximal end of the barrel so as to have the needle fully withdrawn inside the barrel, and thus prevent accidental sticking. In addition or in the alternative, one or more notches may be provided at the distal end of the barrel, so that the needle may be partially and selectively extended from the barrel. By limiting the amount the needle sticks out of the barrel, the retractable needle head can meter the depth of an injection into the tissue of a patient, and thus prevent unnecessary tissue damage. The needle may be used for either intramuscular or intravenous injections.

The needle head is provided with at least one inwardly projecting locking member which mates with an ampoule inserted into the needle head and secures it therein. The locking member is preferably a pawl formed on an interior surface of the needle head and is adapted to mate with a necked down portion of an ampoule.

The invention is preferably provided with a removable needle cover that is adapted to be insertable into the open end of the barrel and serve as the plunger for the hypodermic syringe. Preferably, the needle head has a hub at its external end, and the needle cover is adapted to fit over the hub. The needle cover may further include a flange to facilitate thumb-engaging movement when the needle cover is inserted into the open end of the barrel.

The advantages imparted by the unitary structure of the present invention are a more compact, reduced physical size of an assembled syringe, and importantly, reduced manufacturing cost.

DETAILED DESCRIPTION OF THE DRAWINGS AND THE PREFERRED EMBODIMENT

Figure 1:
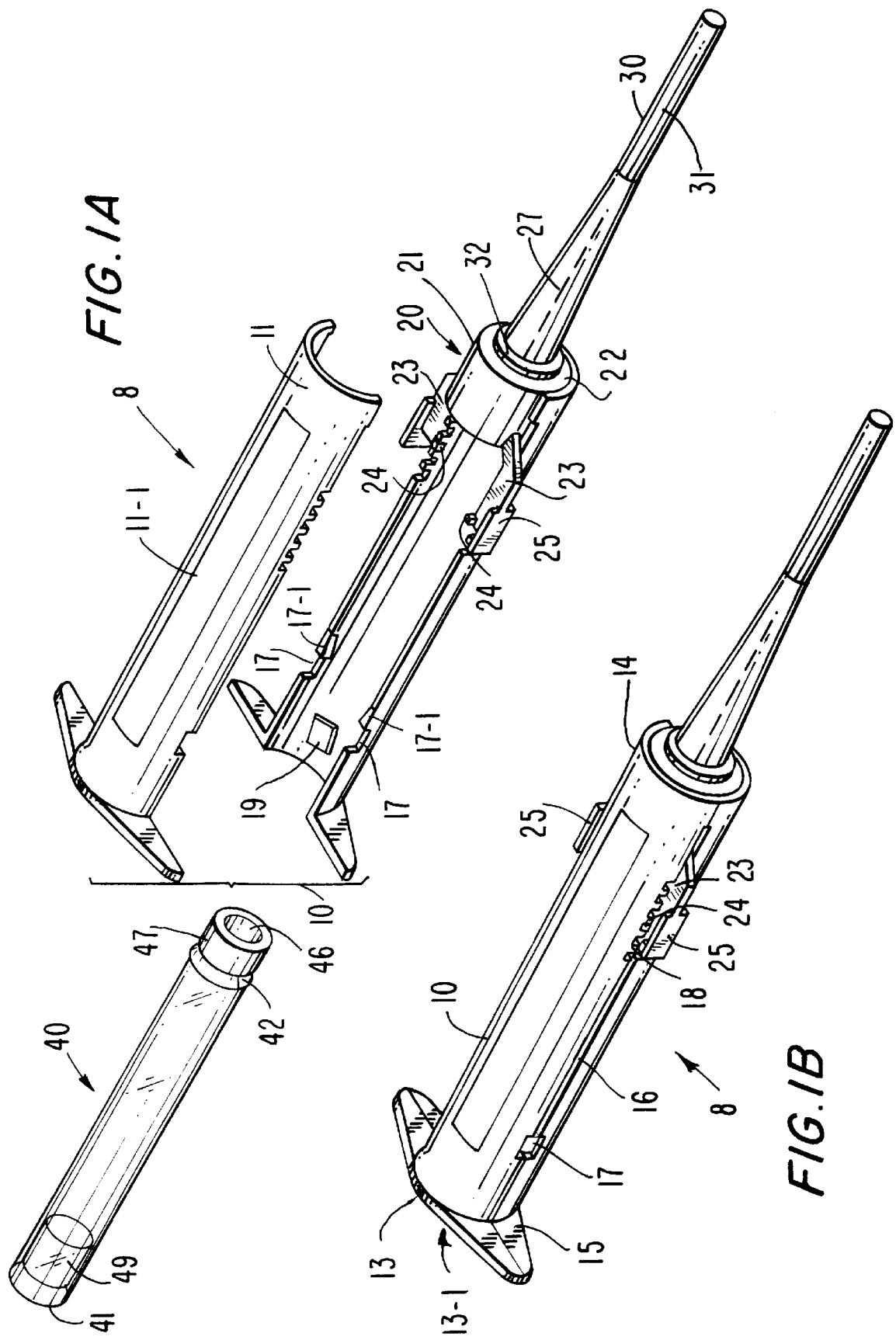
FIG. 1A is an exploded view of the preferred embodiment of the invention before insertion of the ampoule, showing the inventive needle cover covering the needle and the inventive needle head disposed at the distal end of the barrel.
FIG. 1B is a perspective view of FIG. 1A without the ampoule.

The invention comprises a hypodermic syringe having a unitary needle cover and plunger. An embodiment of the invention is illustrated in FIGS. 1–5. As shown in FIGS. 1A–4B, syringe 8 includes a substantially cylindrical hollow barrel 10 having a proximal end 13 and a distal end 14. Proximal end 13 is open, and allows for the insertion of an ampoule 40 containing medicine into the interior portion of barrel 10 via opening 13-1. Flange 15 is provided around the outer periphery of proximal end 13 to facilitate the use of the plunger (as discussed below) and thus the dispensing of medicine. The interior portion of the barrel is preferably sized to receive a standard pre-filled ampoule 40. Barrel 10 may be provided with a resilient flap 19, extending inwards in the interior portion of the barrel, to secure ampoule 40 even though different diameters of the ampoule may be used. In this way, the invention can accommodate any size of ampoules. Barrel 10 is preferably constructed from two halves 11 and 12 which may snap or be glued together in a conventional manner.

One of the halves may be provided with a transparent window 11-1, which acts as a magnifier to allow a user to view more clearly the meniscus of the fluid inside the ampoule. As an alternative, the entire half 11 may be made transparent and serve as a magnifier. The transparent parts of barrel 10 may be made of a known light-transmitting plastic such as styrene.

When the halves 11 and 12 of barrel 10 are fastened together, a longitudinal groove 16 is formed, preferably having a pair of opposed needle locking notches 17 formed close to the proximal end of the barrel and a plurality of opposed needle positioning notches 18 located close to the distal end of the barrel. The purpose of the locking notches 17 and needle positioning notches 18 and groove 16 will be explained below.

Mounted in-between barrel halves 11 and 12 is needle head 20. The body 21 of needle head 20 has a bottom wall 22 through which needle 27 is fixedly mounted (to be discussed in greater detail below). Tabs 23, like rearwardly extending, inwardly resilient arms, are integrally attached to the sides of needle head body 21, and are disposed in groove 16. Needle head 20 may thus slide along groove 16, and the distance needle 27 extends forwarding from barrel 10 may thus be varied and controlled.

Tabs 23 are provided with projections or teeth 24, which fit into and are engaged by notches 17 and 18. When teeth 24 are secured or engaged by one of the notches, the needle head cannot move along groove 16, and the position of the needle is thus fixed. The tabs are preferably flexible or resilient, so that when squeezed, teeth 24 are disengaged from the notches then holding the same. In this fashion, not only can the position of the needle head 20 (and thus needle 27) be set, but it can also be varied.

Locking notches 17 are provided towards the proximal end 13 of barrel 10. When opposed teeth 24 of needle head 20 are engaged in opposed locking notches 17 (see FIG. 4), needle 27 is fully withdrawn inside barrel 10, and accidental needle sticks are prevented. An inwardly tapering projection 17-1 (see FIG. 1A) may be provided on the interior wall of the barrel 10, adjacent to locking notch 17, so that when teeth 24 are engaged in notch 17, it is then difficult to readjust the needle head 20 and needle 27.

Needle position notches 18 are provided towards the distal end 14 of barrel 10. When opposing teeth 24 of needle head 20 are engaged in one pair of opposed notches 18, needle 27 is at least partially extended from barrel 10, (see FIGS. 1–3), and an injection may take place.

Figure 5:
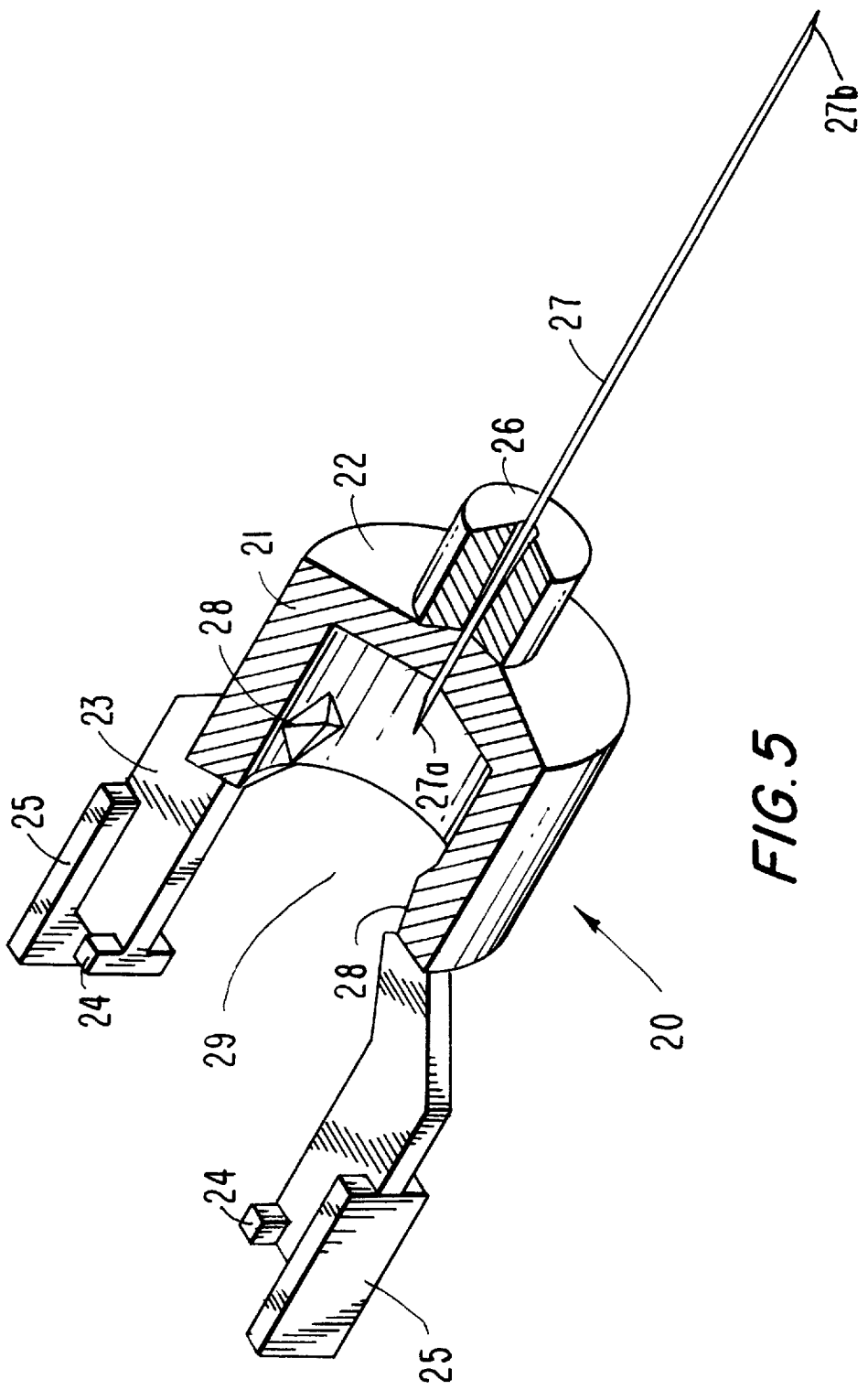
FIG. 5 is an enlarged, partial cut-away and more detailed view of the inventive needle head.

As best illustrated in FIG. 5, needle head 20 is basically cylindrical and is adapted to receive the end of an ampoule 40 (see FIG. 1A) that has a cap 47 disposed thereon. Locking pawls or inward projections 28 are provided on the interior surface of needle head 20 and are adapted to engage the necked-down portion 42 of ampoule 40 when the ampoule is inserted into barrel 10 and needle head 20. These hold the ampoule in place.

Needle 27 preferably is provided with two bevelled ends 27a and 27b and an axial bore (not shown) therethrough. The needle passes through bottom wall 22 of needle head 20 from the interior of the barrel to the exterior, and is preferably mounted in hub 26 for stability. Needle 27 is preferably made from surgical steel or similar material.

As most clearly shown in FIG. 5, bevelled end 27a partially extends into interior portion 29 of needle head 20 and is designed to penetrate the rubber seal 46 of ampoule 40 when the ampoule is inserted into the barrel. Bevelled end 27a only partially extends inside needle head 20, so that no minimal space is formed at the bottom end of the ampoule when the needle pierces the ampoule. In other words, by mounting needle 27 only so far into the barrel that the fully cylindrical part of the needle (below bevelled end 27a) remains inside the needle head, the opening at the very terminus of the needle is disposed at the very end of needle head 20 adjacent bottom wall 22. There is thus no portion of the needle head which is below the opening of the needle, and substantially all of the medicine can be drained from the ampoule without waste.

Needle cover 30 is a hollow tapered cylindrical body that is open at one end and closed at the other. At its open end, needle cover 30 is designed to fit around hub 26 of needle head 20 so that needle 27 is disposed in the interior portion of the needle cover as shown in a dashed line in FIG. 1A. In this position, the needle cover shields needle 27 and prevents it from being damaged, and prevents the needle from accidentally stabbing an unintended individual. Like barrel 10, the open end of needle cover 30 also possesses a flange 32 to facilitate dispensing medicine.

Figure 2:
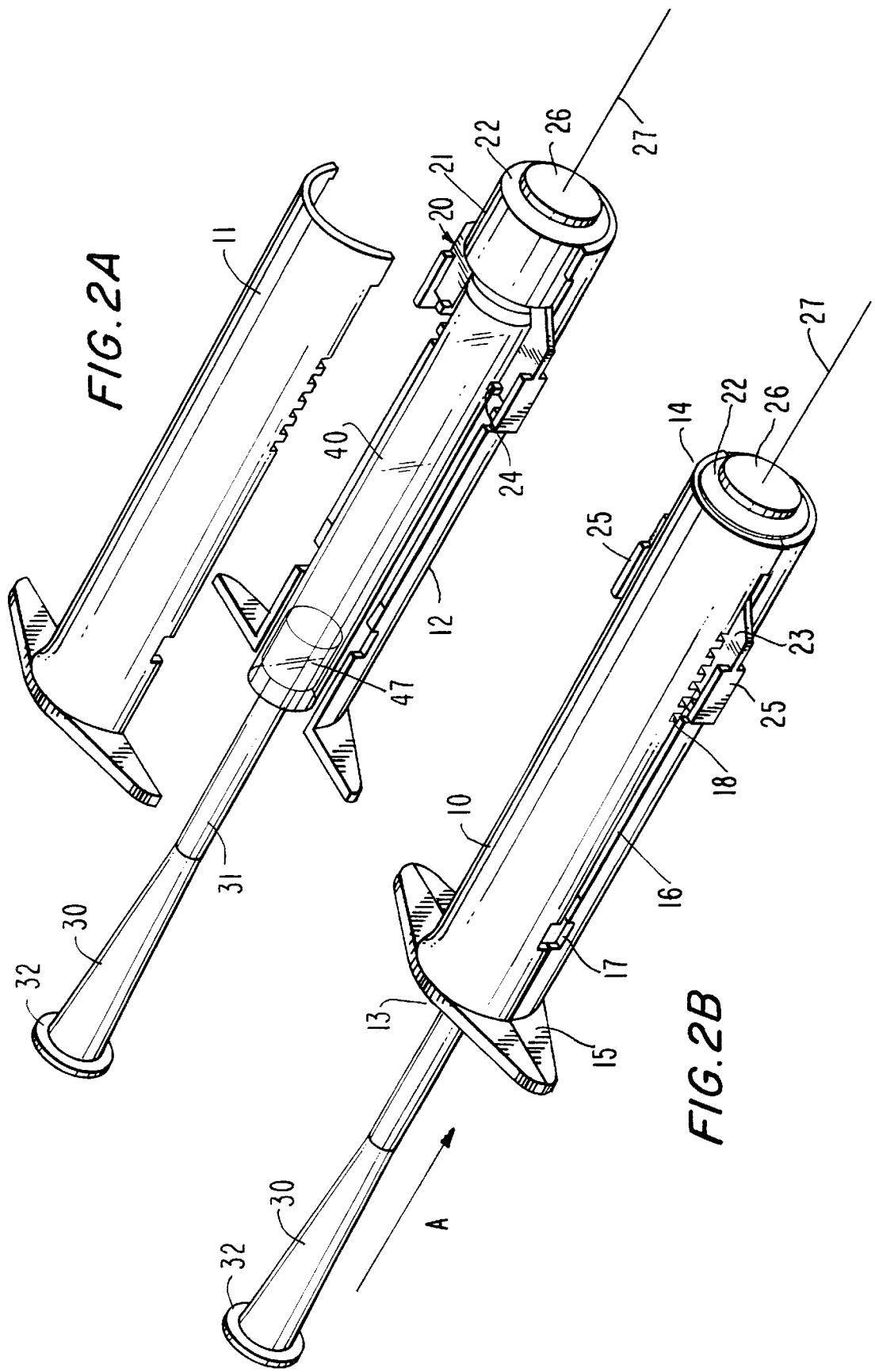
FIG. 2A is an exploded view of the embodiment of FIGS. 1A–B, showing a pre-filled ampoule locked into the barrel, and the inventive needle cover being used as a plunger.
FIG. 2B is a perspective view of FIG. 2A.
Figure 3:
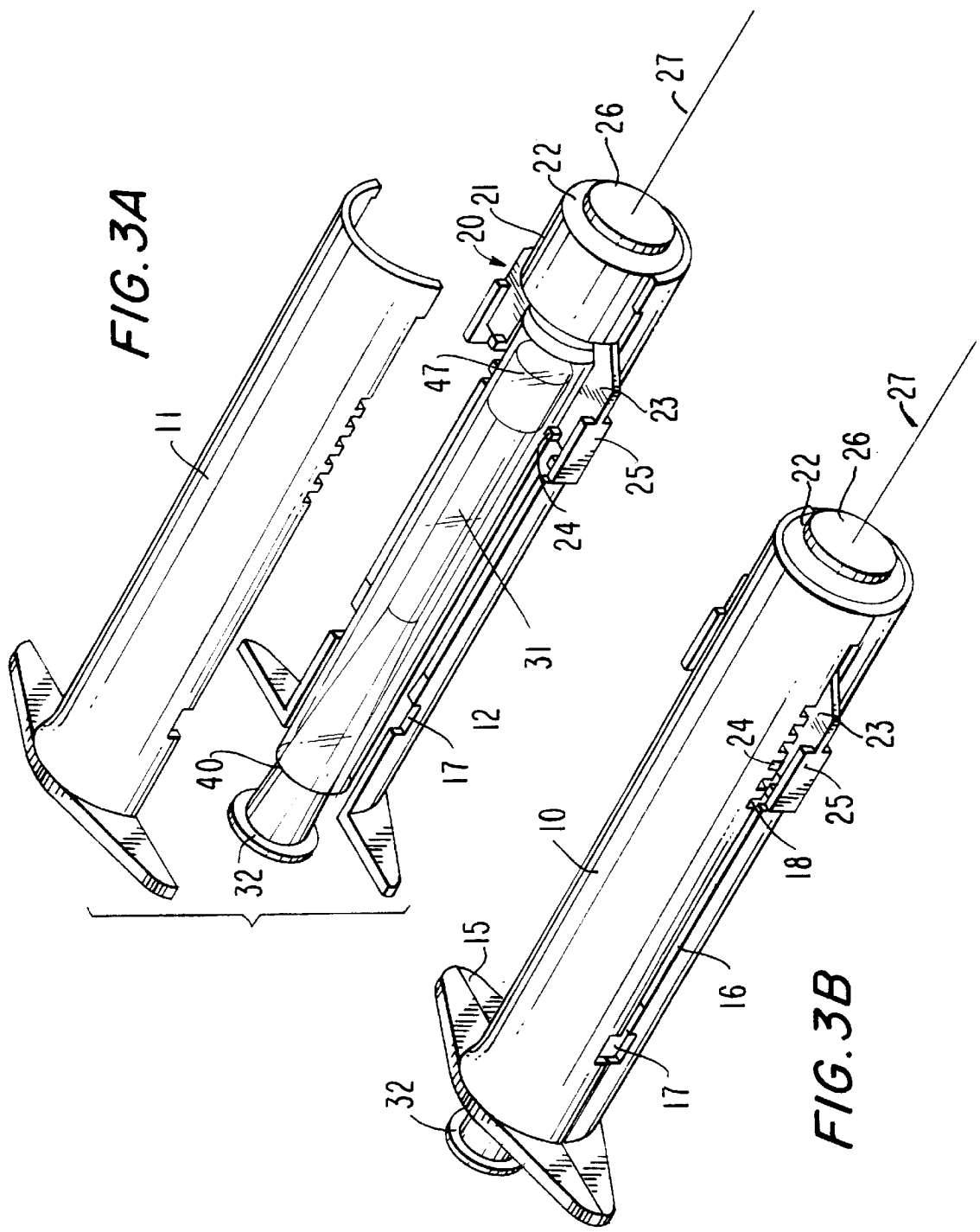
FIG. 3A is an exploded view of the embodiment of FIGS. 1A–2B, showing the invention after medicine has been expelled from the ampoule.
FIG. 3B is a perspective view of FIG. 3A.
Figure 4:
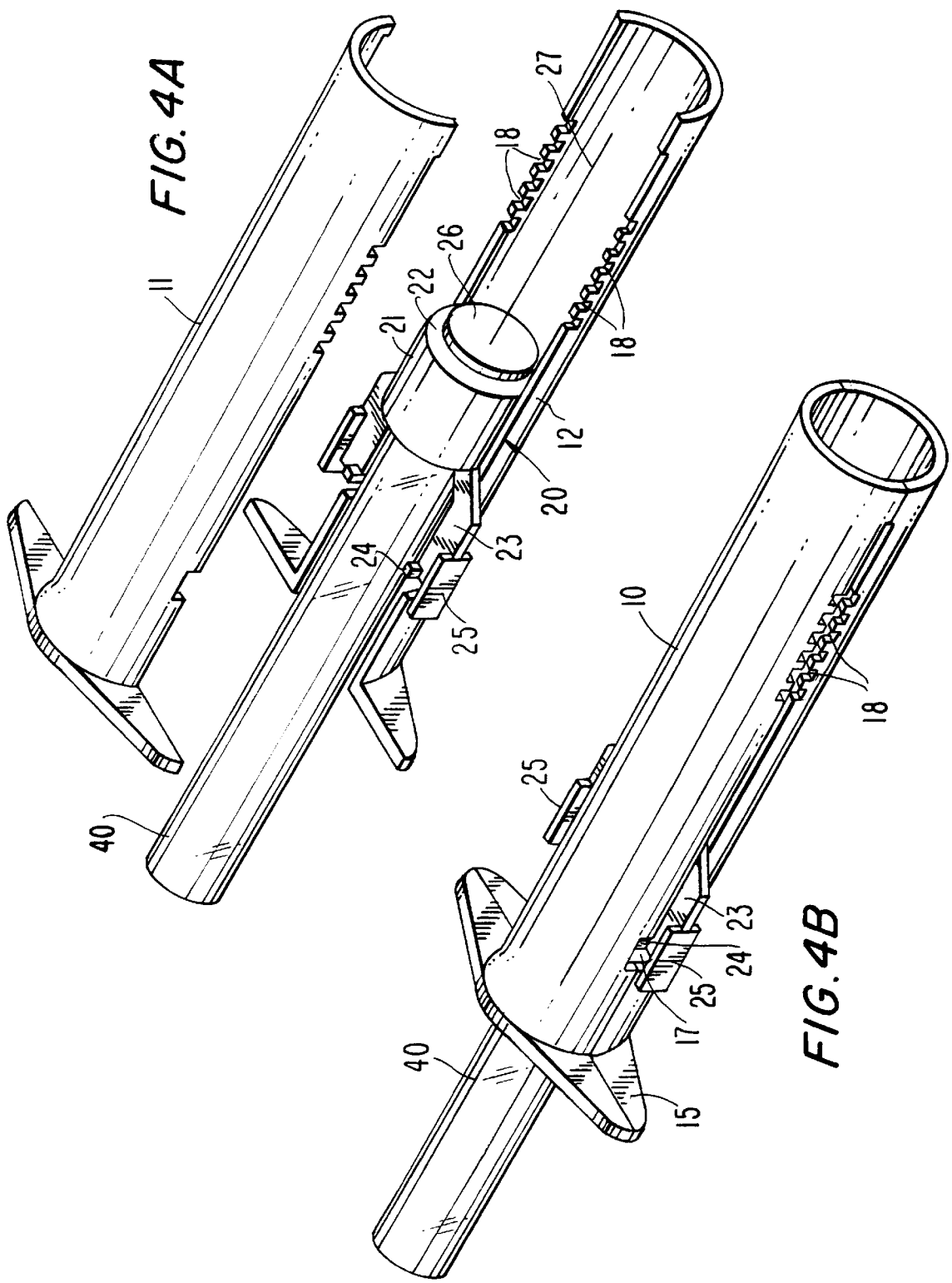
FIG. 4A is an exploded view of the embodiment of FIGS. 1A–3B, showing the inventive needle head being retracted to the locked position after the ampoule is spent.
FIG. 4B is a perspective view of FIG. 4A.

Needle cover 30 also serves as the plunger for syringe 8. The outer diameter of tapered portion 31 of needle cover 30 is sized to be narrower than the inner diameter of ampoule 20 at open end 41. That way, as shown in FIGS. 2 and 3, needle cover 30 can be inserted into open end 41 of ampoule 40 and can abut against rubber stopper 49. In an alternative embodiment, the outer diameter of needle cover 30 is approximately the same as the inner diameter of ampoule 40 thereby enabling a tight fit and proper axial alignment between the needle cover and the ampoule. When force is applied on needle cover 30 in the direction of arrow A in FIG. 2B, rubber stopper 49 pushes the medicine in ampoule 40 out of the barrel via needle 27.

The invention is operated as follows. The assembled syringe 8 of FIG. 1 is sterilized in its package by, for example, gamma radiation. The syringe may come prepackaged with needle cover 30 disposed on hub 26 to protect the needle 27 during shipping. After removal of syringe 8 from the package, an ampoule 40 is inserted into barrel 10 through opening 13-1. Needle head 20 may be disposed down at the distal end 14 of barrel 10, with a pair of opposed teeth 24 engaged in one set of opposed needle positioning notches 18. The precise position of needle head 20 is set by squeezing finger grips 25 of tabs 23, so that needle head 20 may be moved to the proper position. When needle head 20 is in position, grips 25 are released, and teeth 24 spring outwardly to engage one set of opposed notches 18. In this position, needle 27 extends at least partially from barrel 10.

When ampoule 40 is fully inserted, pawls 28 engage the necked-down portion 42 of ampoule 40; bevelled end 27a of needle 27 punctures rubber seal 46 but only partially extends beyond rubber seal 46. The ampoule is secured to the needle head owing to pawls 28, and is secured inside the barrel owing to resilient flap 15 pressing against it. The flap is resilient and allows for the slide into the barrel but reduces the risk of unintended ampoule removal.

Needle cover 30 is then removed from hub 26 and placed inside the open end of ampoule 40 as shown in FIG. 2, so that the closed end of the needle cover abuts rubber stopper 49 of the ampoule. The user of the syringe grasps the underside of flange 15 with two fingers and places his thumb on flange 32 for opposability. Needle cover 30 is pushed downwards in the direction of arrow A, and medicine is expelled from the ampoule via needle 27. The ampoule is then removed from the barrel.

Finger grips 25 are then squeezed, releasing teeth 24 from notches 18. The needle head is slid back towards the proximal end 13 of barrel 10, until teeth 24 line up with a pair of opposed locking notches 17. Grips 25 are released, the teeth resiliently spring outwardly and teeth 24 become securely engaged in notches 17. Inwardly directed projection 17-1 insures that needle head 20 will not be accidentally dislodged from this position. In this position, the needle is fully withdrawn inside barrel 10, and accidental sticking is prevented. The needle cover can be removed from the open end of the barrel and may re-cover hub 22 and thus needle 27 to further prevent inadvertent injury.

Having described the invention with regard to specific embodiments, it is to be understood that the description is not meant as a limitation, and that such further variations or modifications may be apparent or may suggest themselves to those skilled in the art. It is intended that the present invention cover such variations and modifications as fall within the scope of the appended claims.

What is claimed is:

1. A hypodermic syringe, comprising:
   a barrel having an interior portion adapted to receive an ampoule, said barrel having first and second ends and a longitudinal groove having a plurality of notches formed substantially at said first end of said barrel;
   a needle head, movably mounted in said barrel adapted to move along said longitudinal groove of said barrel, having at least one tab, extending from said needle head and disposed in said longitudinal groove of said barrel, adapted to allow adjustment of a position of said needle head along said barrel, said tab having at least one projection, said notches being adapted to engage said projection to lock said needle head into predetermined positions; and
   a needle, having an axial bore therethrough in communication with said interior portion of said barrel, fixedly mounted in said needle head,
   wherein when said projection is engaged in one of said plurality of notches, said needle partially extends out from said barrel.

2. A hypodermic syringe according to claim 1, wherein said tab is resilient and can be withdrawn into said interior of said barrel when pressure is applied to said tab.

3. A hypodermic syringe according to claim 1, wherein said tab is resilient and withdraws into said interior of said barrel when pressure is applied to said tab, thereby disengaging said projection from said notch.

4. A hypodermic syringe according to claim 3, wherein said notch is disposed at said second end of said barrel.

5. A hypodermic syringe according to claim 1, further comprising a protuberance disposed on an interior wall of said barrel adjacent said notch.

6. A hypodermic syringe according to claim 5, further comprising a protuberance disposed on an interior wall of said barrel adjacent said second notch.

7. A hypodermic syringe according to claim 5, wherein said tab comprises a flange, disposed on an outer portion of said tab, adapted to facilitate application of inward pressure on said tab.

8. A hypodermic syringe according to claim 1, wherein said needle head further comprises a body having an open end and a bottom wall forming an interior volume adapted to receive an end of an ampoule, said needle extending through said bottom wall and in to fluid communication with said interior volume.

9. A hypodermic syringe according to claim 8, wherein said needle head further comprises at least one locking pawl formed on an interior surface of said needle head adapted to mate with a necked down portion of an inserted ampoule.

10. A hypodermic syringe according to claim 1, wherein said needle comprises first and second bevels terminating in points disposed at opposite ends of said needle, wherein said first bevel partially extends into said interior volume of said needle head through said bottom wall.

11. A hypodermic syringe according to claim 1, further comprising a needle cover having an internal space, said needle cover adapted to fit on an external portion of said needle head and house said needle within said internal space, said needle cover also adapted to be removable from said needle head and insertable into said second end of said barrel thereby becoming a plunger for the hypodermic syringe.

12. A hypodermic syringe according to claim 11, wherein said needle head further comprises a hub disposed on said external portion of said needle head, and said needle cover is adapted to fit over and engage said hub.

13. A hypodermic syringe according to claim 11, wherein an outer diameter of said needle cover is narrower than an inner diameter of an ampoule inserted into said barrel.

14. A hypodermic syringe according to claim 11, wherein said needle cover further comprises a flange, provided at one end of said needle cover, adapted to facilitate movement of said needle cover when it is inserted into said second end of said barrel.

15. A hypodermic syringe according to claim 1, further comprising a resilient flap, disposed in said interior portion of said barrel at said second end of said barrel, adapted to locate an ampoule inserted into said barrel.

16. A hypodermic syringe, comprising:

a barrel having an interior portion adapted to receive an ampoule, said barrel having first and second ends and a longitudinal groove having a first plurality of notches disposed substantially at said first end of said barrel and a second notch disposed substantially at said second end of said barrel;

a needle head, movably mounted in said barrel adapted to move along said longitudinal groove of said barrel, having at least one tab, extending from said needle head and disposed in said longitudinal groove of said barrel, adapted to allow adjustment of a position of said needle head along said barrel, said tab having at least one projection, said first and second notches being adapted to engage said projection to lock said needle head into predetermined positions; and a needle, having an axial bore therethrough in communication with said interior portion of said barrel, fixedly mounted in said needle head, wherein when said projection is engaged in one of said first plurality of notches, said needle partially extends out from said barrel, and wherein when said projection is engaged in said second notch, said needle is fully contained within said barrel.

17. A hypodermic syringe, comprising:

a barrel having an interior portion adapted to receive an ampoule, said barrel having first and second ends;

a needle head, movably mounted in said barrel adapted to move along said barrel; and a needle, having an axial bore therethrough in communication with said interior portion of said barrel, fixedly mounted in said needle head;

said needle head further comprising:

a body having an open end and a bottom wall forming an interior volume adapted to receive an end of an ampoule, said needle extending through said bottom wall and in communication with said interior volume; and at least one locking pawl formed on an interior surface of said needle head adapted to mate with a necked down portion of an inserted ampoule.

* * * * *